US012564708B2

(12) United States Patent
    Grant et al.

(10) Patent No.:  US 12,564,708 B2
(45) Date of Patent:      Mar. 3, 2026

(54) SINGLE-USE CASSETTE ASSEMBLY

(71) Applicant: AVAXMED LIMITED, Abingdon (GB)

(72) Inventors: David Grant, Faringdon (GB); Pascal Launois, Dublin (IE); Joshua Coyne, Wicklow (IE); Owen Ryan, Wicklow (IE)

(73) Assignee: AVAXMED LIMITED, Abingdon (GB)

( * ) Notice: Subject to any disclaimer, the term of this patent is extended or adjusted under 35 U.S.C. 154(b) by 1024 days.

(21) Appl. No.: 17/295,930

(22) PCT Filed: Nov. 22, 2019

(86) PCT No.: PCT/GB2019/053303
    § 371 (c)(1),
    (2) Date: May 21, 2021

(87) PCT Pub. No.: WO2020/104812
    PCT Pub. Date: May 28, 2020

(65) Prior Publication Data
    US 2022/0008704 A1      Jan. 13, 2022

(30) Foreign Application Priority Data
    Nov. 22, 2018    (GB) ..................................... 1819059

(51) Int. Cl.
    *A61M 37/00*        (2006.01)
(52) U.S. Cl.
    CPC ... *A61M 37/0069* (2013.01); *A61M 2205/123* (2013.01); *A61M 2205/273* (2013.01)

(58) Field of Classification Search
    CPC ........ A61M 37/0069; A61M 2205/123; A61M 2205/273; A61M 5/50; A61M 5/30; A61B 17/20
    See application file for complete search history.

(56) References Cited

U.S. PATENT DOCUMENTS 6,123,688  A     9/2000  Botich et al.
    8,574,188  B2    11/2013  Potter et al.
              (Continued)

FOREIGN PATENT DOCUMENTS

EP        2835146  A1     2/2015
    WO        9510314  A1     4/1995
              (Continued)

OTHER PUBLICATIONS

International Search Report and Written Opinion for PCT Application No. PCT/GB2019/053303 mail date May 2, 2020, 11 pages.
              (Continued)

*Primary Examiner* — Dung T Ulsh
*Assistant Examiner* — Fatimata Sahra Diop
(74) *Attorney, Agent, or Firm* — Maine Cernota & Curran

(57) ABSTRACT

The invention relates to a single-use cassette assembly for use in a reusable solid dose formulation delivery actuator device. Such improvements permit delivery of at least one therapeutic or prophylactic compound, or a solid dose formulation including, for example, a vaccine comprising the same with improved safety and reliability. The invention further concerns an improved needle-free method for delivering at least one therapeutic compound or a formulation comprising the same.

19 Claims, 5 Drawing Sheets

1

(56)                    References Cited

U.S. PATENT DOCUMENTS

| | | | |
|---|---|---|---|
| 2004/0094147 A1* | 5/2004 | Schyra .................... A61M 5/50 128/200.14 |
| 2009/0030442 A1* | 1/2009 | Potter .............. A61B 5/150916 606/182 |
| 2010/0076374 A1 | 3/2010 | Landau |
| 2014/0018725 A1* | 1/2014 | Potter ................. A61M 31/007 604/59 |
| 2014/0290792 A1 | 10/2014 | Avery et al. |
| 2018/0064877 A1 | 3/2018 | Schneider et al. |
| 2021/0060253 A1* | 3/2021 | Dahmani .......... A61M 5/31558 |

FOREIGN PATENT DOCUMENTS

| | | |
|---|---|---|
| WO | 2003023773 A1 | 3/2003 |
| WO | 2004014468 A1 | 2/2004 |
| WO | 2006082439 A1 | 8/2006 |
| WO | 2011068809 A1 | 6/2011 |
| WO | 2012098356 A1 | 7/2012 |
| WO | 2014037946 A1 | 3/2014 |
| WO | 2017033193 A2 | 3/2017 |
| WO | 2017068351 A1 | 4/2017 |

OTHER PUBLICATIONS

GB Search Report for Patent Application No. GB1819059.5 mail date May 8, 2019.

* cited by examiner

SINGLE-USE CASSETTE ASSEMBLY

RELATED APPLICATIONS

This application is a national phase application filed under 35 USC § 371 of PCT Application No. PCT/GB2019/053303 with an International filing date of Nov. 22, 2019, which claims priority of GB Patent Application 1819059.5, filed Nov. 22, 2018. Each of these applications is herein incorporated by reference in its entirety for all purposes.

FIELD OF THE INVENTION

The present invention relates to improvements in solid dose formulation delivery, in particular, to vaccine delivery cassettes with enhanced functionality. In particular, the invention relates to a single-use cassette assembly, comprising a re-use prevention mechanism.

More particularly, the invention relates to a single-use cassette assembly for use with a reusable solid dose formulation delivery actuator device. Such improvements permit delivery of at least one therapeutic compound, such as a vaccine or a formulation comprising the same, with improved safety and mode of action. The invention further concerns an improved needle-free method for delivering at least one therapeutic compound or a formulation comprising the same.

BACKGROUND TO THE INVENTION

Parenteral delivery is one of the more efficient routes for delivery of a therapeutic compound when compared to other standard routes such as oral or pulmonary delivery. Parenteral administration is most commonly undertaken using a needle and syringe as a delivery system with the therapeutic compound in a liquid form. However, needle-based methods remain disadvantageous for a variety of reasons including the issues of patient compliance and waste disposal safety. In addition, liquid formulations are typically less stable in aqueous form than in a solid dose form and a large proportion of therapeutic or prophylactic agents are poorly soluble, often resulting in the production of sub-optimal formulations.

Solid dose formulations have been administered by accelerating powdered solid dose formulations to a velocity at which they can penetrate the outer layers of the skin. Such systems typically employ powdered solid dose formulation particles of less than 100 microns in diameter and require a velocity of several hundred metres per second in order to penetrate human tissue. Other systems use solid rods or splinters of a therapeutic compound that can be pushed at a relatively lower velocity into the skin without the requirement for a needle.

The present applicants have successfully developed their own needle-free parenteral delivery device technology used as a means for introducing solid dose therapeutics, including proteins and vaccines. This is described in at least International applications WO2003/023773, WO2004/014468, WO 2006/082439, WO 2006/082439 and WO2017/068351.

The originating methods include delivering compounds or formulations by penetrating the skin with a pioneer projectile and introducing behind the projectile, the therapeutic of interest in a liquid, semiliquid or solid dose form, or having the therapeutic of interest included as part of the projectile itself. Devices for needle-free injection are described by the present applicants, for example U.S. Pat. No. 8,574,188 describes a mechanism which generates a force to cause a striker to travel along a guide and a separate component comprising a casing having an aperture in which is mounted an ejector pin and a package comprising said projectile/formulation with a means for triggering the device; the housing has an end which is in operative communication with the component such that in use the striker will contact the ejector pin and the injectate will be pushed out of the casing as a single unit. The mechanism is therefore capable of generating the force and comprises a power source for initiating or assisting the pushing of the injectate from the device. A large headed ejector pin (also referred to as a cassette/drive pin) comprising a flat head and an elongate body is positioned behind the injectate so that when the ejector pin is contacted, in use, by a striker the injectate is pushed along the central aperture or chamber and out into the patient. The disposable assembly is loaded into the front end of the inner housing of the actuating device.

Actuation is triggered with a push button or by pushing the device against the skin. When actuated, the striker or hammer travels along the striker guide until it contacts the head of the ejector pin with a force that causes the injectate to pierce the skin. The ejector pin continues to push the formulation into the patient to the required depth, which is determined by the length of the injectate and the extent to which it is pushed by the ejector pin.

In the method described, it is possible to penetrate the skin with the therapeutic compound administered at a low velocity. By low velocity is meant less than 100 m/s. Preferably the velocity is less than 10 m/s. Since the injectate is pushed at a low velocity rather than fired at a high velocity it is possible to ensure that the dosage is always delivered to the correct (and same) depth under the skin. This means that the system can be used on different skin types and skin locations and the dosage will still be delivered to the same depth.

With this type of user operated reusable device, known as an actuator, it is desirable that accidental re-actuation or re-use of the component, known as the cassette, which contains the injectate prior to delivery, is avoided in order to ensure the safety of both the user and the recipient. Prior art devices have a limited function in that the status of the cassette (i.e. used or unused) could only be identified visually. It remains possible that a spent cassette could be re-connected onto the actuator, at least partially, and re-actuated when the actuator mechanism was re-set.

The present invention therefore comes about from a desire to improve such operating systems further to provide a reliable, safe and patient compliant device for delivery of vaccines and therapeutics and solid dose agents.

SUMMARY OF THE INVENTION

In a first aspect of the invention an improved cassette assembly is provided for use with a delivery device, 'actuator', of the type described in the prior art as well as improved devices described concurrently in the applicant's published patent applications.

The invention concerns a single use cassette assembly for use with a parenteral delivery actuator and configured to allow operative connection therewith, the cassette assembly comprising: a re-use prevention mechanism including at least: one or more lockout clips having a first configuration which permits use of the cassette with the actuator and in a second configuration which prevents re-use with the actuator.

In embodiments the first configuration is a non-extended state and the second configuration is a naturally biased extended state. Preferably, in some embodiments the re-use prevention mechanism comprises 2, or optionally 4, lock-out clips.

The cassette assembly may further comprise a cassette body for engaging the actuator device and a carriage housed within the cassette body, the carriage having a channel configured to releasably retain a solid dose formulation.

In embodiments each lockout clip has a first end clamped to the cassette body and a second end comprising a hook and optionally the cassette body comprises a hook retaining edge for engaging the hook. The carriage and cassette body may comprise aligned apertures in which the lockout clips sit.

In embodiments, the lockout clips remain in the first configuration or non-extended state until the cassette is actuated forcing the lockout clips to deflect outwardly to their second configuration or naturally biased extended state hooking the cassette body and preventing re-use of the cassette with the actuator. Optionally the lockout clips in their second configuration further prevent reinsertion of the cassette into the actuator to an extent possible to cause actuation.

Where the carriage and cassette body comprise aligned apertures through which the lockout clips sit, the lockout clips remain in a non-extended state until the cassette is actuated, the action of which causes the lockout clips to deflect outwardly via the apertures to their naturally biased extended state where they hook onto the hook retaining edge of the cassette body, in which state they prevent full rein-sertion of the cassette into the actuator and therefore prevent re-activation of the cassette.

In embodiments, the cassette lockout clips preferably comprise spring steel sheet-metal or other shape-memory material so that the natural shape of the clips is always biased and flexes towards the extended position.

In embodiments the invention is configured to have further useful functionality.

In this regard in some embodiments the cassette further comprises a cassette pin positioned rearwardly from the solid dose and prior to actuation of the device temporarily secured thereat by one or more pin release clips, thereby preventing forward motion being transferred to the solid dose relative to the carriage.

The applicants determined that devices of the prior art comprised arrangements in which the solid dose vaccine or therapeutic agent or formulation was held in the cassette by flexible arms which simply allowed release of the solid dose when the pin applied any forward motion. Unfortunately, this mechanism was deemed unreliable since premature release of the solid dose could be possible if the pin moved forward during storage. Thus, unintentional movement of the pin even when the cassette is not actuated could release the solid dose.

Thus, to ensure that the solid dose does not get released prematurely, the applicants have devised a useful solution to ensure the retaining/holding and release functions are con-trolled by two independent features of the device. As defined in the invention, the solid dose is held, preferably by compression, between the two carriage jaws. The compres-sive forces may generate friction to retain the solid dose during storage, transport and actuation until point of formal release. Further, a cassette pin is inserted behind the solid dose and prior to actuation is held in place by one or more pin release clips.

When the cassette is in the pre-actuation status, the pin release clips are prevented from deflecting out as they are held by the cassette body's inner restrictive diameter. The pin release clip geometry, which maybe V-shaped, controls the axial position of the pin inside the carriage to ensure no forward motion can be transferred to the solid dose during its lifetime before actuation e.g. by inherent minor forward motion of the pin (not caused by actuation of the device). In some embodiments the pin release clips latch onto a corre-sponding pin groove during the assembly of the pin into the carriage.

In embodiments the carriage is releasably secured within the cassette body by pre-release legs. The carriage is held in place within the cassette body by the pre-release legs before actuation. These pre-release legs keep the carriage, pin, solid-dose assembly in place inside the cassette body in a fixed axial position.

In some embodiments the cassette body further defines pre-release clip windows in which the pre-release legs on the carriage sit prior to actuation. During the actuation sequence, the pre-release legs are deflected into the pre-release clip windows in the cassette body, when getting into contact with clips, which may be metal clips, housed within the actuator. At this point of the actuation sequence, the carriage-pin-dose assembly is held together by the pin release clips to ensure they move together and there is no premature release of the solid dose from the carriage.

In some embodiments the carriage is adapted to be guided by rails to ensure the solid dose does not rotate ahead of being release for penetration. The carriage may typically comprise carriage jaws and a cassette opening cone. When formal actuation occurs as the carriage is accelerated for-ward, the carriage jaws open when hitting the cassette opening cone, releasing the lateral holding force applied to the solid dose. However, in accordance with the present invention, when the solid dose is released, the carriage pin release clips deflect out when they reach the pin release window. This action is due to a pin groove ramp angle and the force applied by the spindle onto the pin when the carriage decelerates. The timing of the release of the pin ensures that the solid dose is released by the carriage jaws only immediately before it is pushed forward by the released pin. At the point of release, the solid dose is guided in the front by the cassette body exit hole and in the back by the carriage jaws. The opened jaws allow for the pin to move forward with minimum friction.

The present applicant considers that even though prior art cassettes are used whose use-status could be identified visually, they could inadvertently be reconnected with the actuator and the cassette pin re-actuated. The "used" status cassette and other such solutions described by the prior art may not always be sufficient to prevent re-use. However, the present invention, incorporating the lockout clips, serves to prevent accidental re-use. Further still, in embodiments the cassette comprises a solid dose viewing window or aperture to enable the injectable solid dose formulation to be viewed prior to injection. After injection, the cassette internal com-ponents fill this window with a colour coding showing the status of a used cassette. In addition, in some embodiments, the lockout clips, or part thereof, may themselves be located within a space defined by the viewing window.

The invention further extends to a single use cassette assembly wherein the solid dose is an implant or splinter. Preferably, the solid dose comprises a vaccine.

The invention further extends to a single use cassette assembly where the assembly is for use with a needle-free parenteral delivery actuator.

The invention also extends to a kit comprising a solid dose delivery actuator and a single use cassette assembly as described herein. In embodiments, the actuator is needleless.

BRIEF DESCRIPTION OF THE DRAWINGS

The various aspects of the invention will now be described, by way of example only, with reference to the following drawings.

FIG. 4b shows an isometric view of the same actuated cassette in FIG. 4a;

DETAILED DESCRIPTION

The cassette assembly of the invention (1) is typically used with and actuated by a parenteral needle-free solid dose delivery device of the type described in the applicant's earlier patent publications (as referred to herein above), hereafter referred to as an actuator.

The cassette is adapted to deliver a solid dose formulation containing a therapeutic compound, such as a vaccine, by pushing the solid dose into a human or animal body using the energy supplied by an actuator. In such use, cassette assemblies which house the solid dose formulation are preferred to be consumable, non-reusable cartridges. Patient safety is enhanced by the advantages the cassette assembly disclosed herein confers to the overall delivery mechanism.

Figure 1:
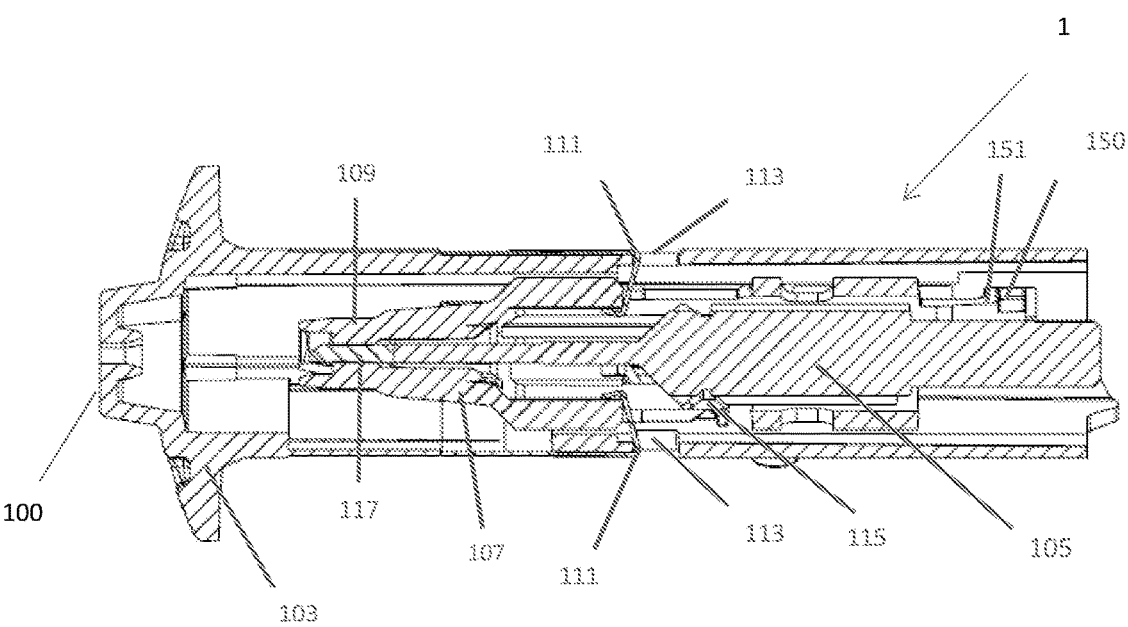
FIG. 1 shows a cassette assembly in cross-section, according to an embodiment of invention in an unactuated state.
Figure 2:
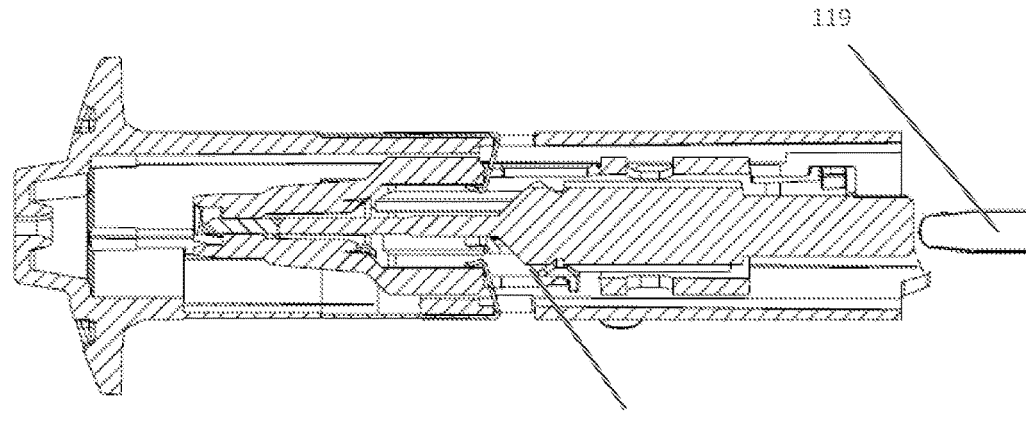
FIG. 2 shows the cassette assembly of FIG. 1 in the pre-actuated state, with the actuation spindle in alignment.

FIG. 1 shows a cassette assembly (1), as provided in one embodiment of the invention, in a non-actuated state which houses a solid dose formulation (117).

Such a needle-free delivery device (shown partly in FIGS. 4c, 5 and 6) comprises housing components including a body (200). During use, the cassette assembly containing the solid dose is connected into the front section of the actuator body and the cassette and actuator are in operative communication with one another. The actuator houses a force generating means, such as a spring.

During use, the front section houses the connected cassette assembly (1) as per the invention, as described herein, including a solid dose formulation (117), and a means for transmitting the force provided from the force generating means, in order to push the solid dose formulation (117) from the cassette assembly (1) into the body via displacement of the cassette pin (105).

In the first unactuated mode, the cassette assembly (1) is connected to the front section of the actuator (not shown) and is axially orientated.

The cassette body (103) of the assembly houses a cassette carriage (107) which, in turn, houses a centrally positioned cassette pin (105) and a solid dose formulation (117). These components are initially fixed in position within the cassette body.

The carriage is held in position within the cassette body by pre-release legs (151) sitting within pre-release windows (150) in the cassette body. The carriage is releasably secured within the cassette body by pre-release legs. The carriage is held in place within the cassette body by the pre-release legs before actuation. These pre-release legs keep the carriage, pin, solid-dose assembly in place inside the cassette body in a fixed axial position until point of actuation and release/delivery is required.

The carriage includes two jaws (109) located in the front of the carriage (107). The solid dose formulation (117) is held by compression acting on its external surface. In particular, the lateral compressive forces of the jaws generate sufficient friction to retain the solid dose (117) in this position within the carriage (107) during storage and general movement or transport of the device, until the point of actuation and release/delivery is required.

Two or more lockout clips (111) are clamped onto an external surround of the cassette body (103) each clip comprises a hooking element. In their non-deflected, pre-actuation position the hooking element of the clip is releasably engaged onto an inner surface of the carriage (107) through an opening or window (113) in the cassette body (103). However, the natural shape of the clips is in the extended or deflected position, which itself allows a consistent holding force of the hooking element. Cassette lockout clips (111) are made, for example, from spring steel sheet metal.

The cassette pin (105) is positioned behind the solid dose formulation (117) abutting a rear-facing end thereof. The pin is initially held in place within the carriage (107) by a set of pin release clips (115). The pin release clips are latched onto corresponding groove or grooves in the pin during the assembly of the cassette (1).

In the pre-actuated mode, the pin release clips (115) cannot deflect/extend out as they are held and or constricted by the inner diameter size of the cassette body (103). The pin release clips are 'V' shaped to control the axial position of the cassette pin (105) inside the carriage (107). The secure pin ensures no unintentional forward motion is transferred to the solid dose relative to the carriage prior to intentional controlled actuation of the device.

The cassette pin and actuator are in operative communication through a spindle (not shown). The spindle tip (119) is adapted to push the cassette pin upon actuation which in turn pushes the solid dose formulation from the cassette assembly into the human or animal body.

In operation, once the cassette is inserted into the actuator it can be actuated by a user holding the device about its housing and pressing the device against the patient's skin. This causes the skin to be tensioned and the cassette to slide up inside the front section of the actuator. This sliding action is used to prime and ultimately cause the spring in the actuator to be compressed until the necessary drive force is reached and the full mechanism actuates.

When actuation of the device is fully initiated the spindle (119) pushes the carriage (107), cassette pin (105) and solid dose (117) forward. In examples the front end of the actuator may include a shape (not shown) to release the pre-release legs (151) of the carriage from the pre-release window (150) on the cassette body. As the carriage is accelerated forward, the carriage jaws (109) retaining the solid dose hit the opening cone of the cassette body (103) releasing the solid dose. At the same moment the pin release clips (115) reach the pin release windows (113) on the cassette body and are pushed into them allowing the cassette pin to move forward relative to the carriage, thus enabling it to push the solid dose into the skin. The carriage-pin-solid dose assembly may be guided by rails to prevent rotation of the mechanism. The timing of the release of the pin ensures that the solid dose is released from the carriage jaws before it is pushed forward by the cassette pin. The opened jaws allow for the pin to move forward with minimum friction. The solid dose penetrates the skin as the required acceleration and the required velocity is generated from the actuation mechanism of the device.

Figure 3:
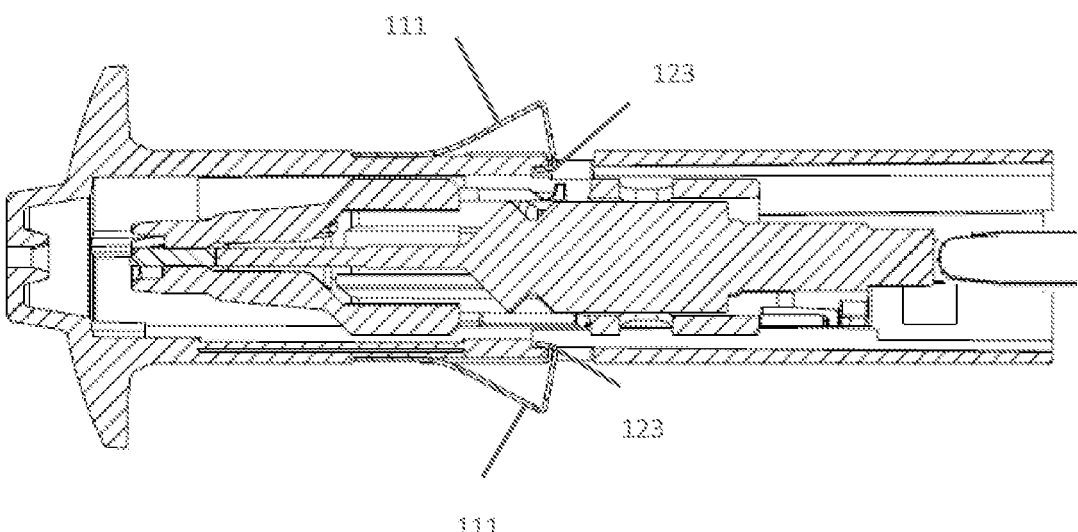
FIG. 3 shows the cassette assembly of FIG. 2 moved to an actuating position with the lockout clips activated and the carriage moved within the cassette body.

As shown in FIG. 3, during actuation the carriage moves forward within the cassette assembly releasing the hook of the lockout clips from the inner surface of the carriage. This allows the clips to freely deflect out and assume their naturally extended state. The clip hooks are at this point engaged with a hook retaining edge (123) on the cassette body (103).

Figure 4A:
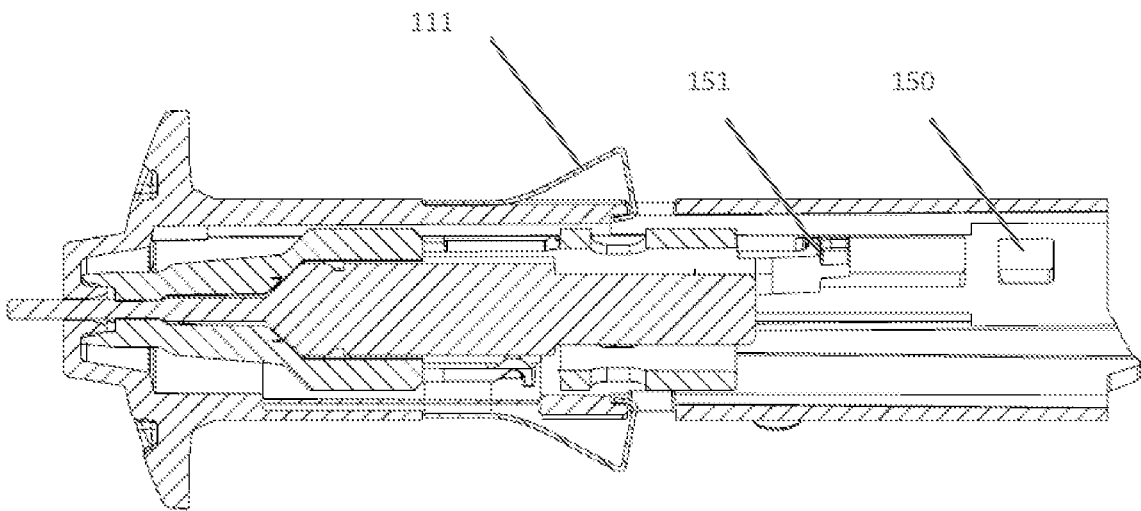
FIG. 4a shows the cassette in an actuated state.
Figure 4B:
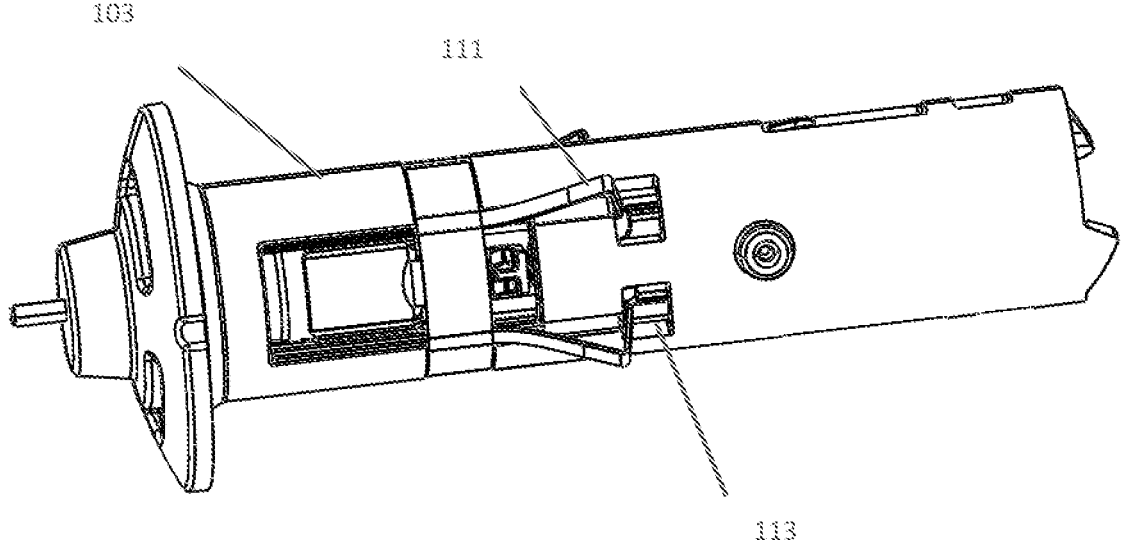
Figure 4C:
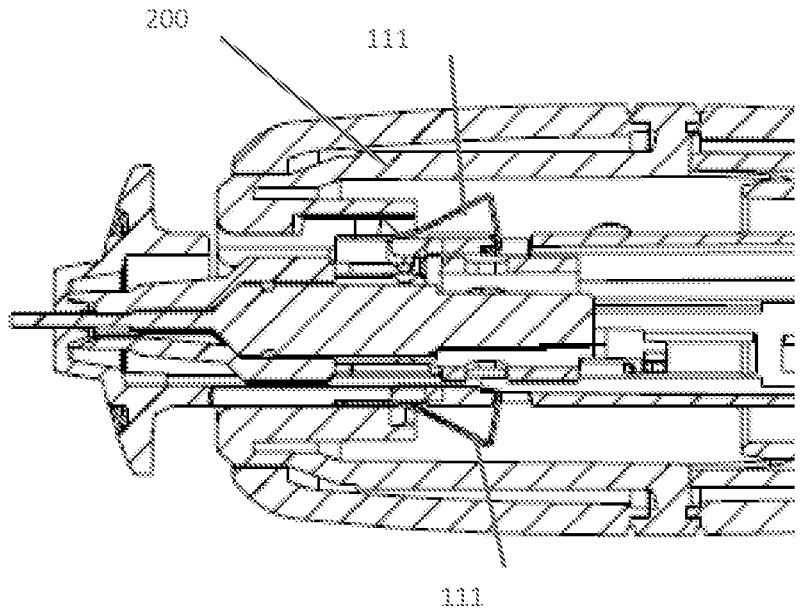
FIG. 4c shows the cassette of FIG. 4a housed relative to the actuator body immediately after actuation.

Immediately after actuation the cassette is housed within the body of the actuator with the lockout clips in their naturally extended state as shown in FIG. 4c.

Figure 5:
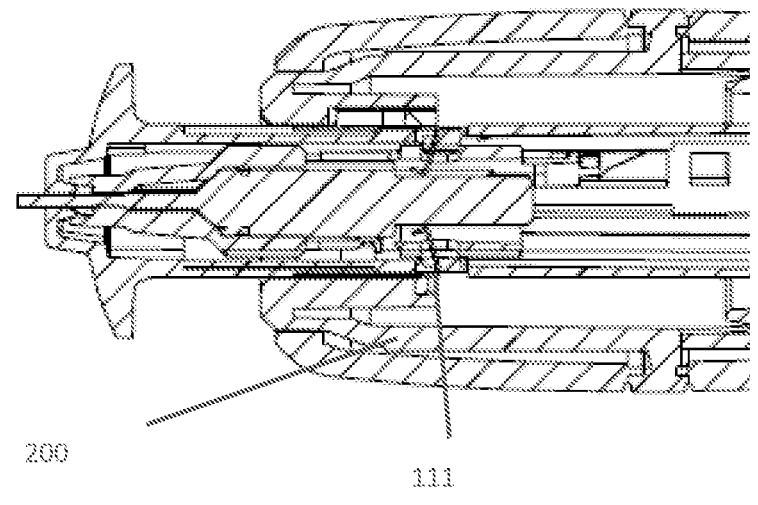
FIG. 5 shows the transitional release position of the used cassette from the actuator body with the lockout clips in a folded configuration to allow release of the cassette assembly from the actuator.

FIG. 5 shows how the lockout clips easily temporarily deflect inwards with minimum force to clear the opening diameter of the actuator in order to remove the cassette from the actuator immediately after its first actuation.

Figure 6:
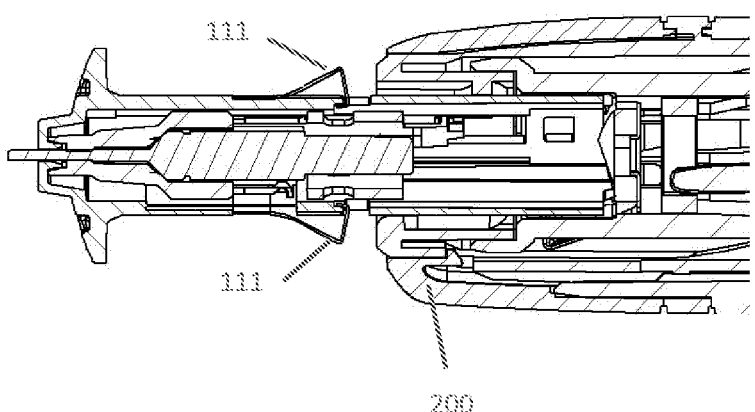
FIG. 6 shows the cassette in an actuated state after it has been released from the skin and is ready for removal and the cassette lockout clips have exited the actuator housing and are preventing re-insertion and therefore re-actuation.

However, as shown in FIGS. 4a, 4b and 6 when the cassette is in the most forward position, the deflected lockout clips do not allow for the cassette to be actuated again, even when the cassette is pressed against the skin as they prevent the cassette body from sliding up inside the front section of the actuator, thus preventing the actuator mechanism from being primed and actuated.

The invention claimed is:

1. A single use cassette assembly for use with a parenteral delivery actuator and configured to allow operative connection therewith, the cassette assembly comprising: a re-use prevention mechanism including at least: a cassette body with one or more lockout clips having a first configuration, which permits use of the cassette body with the actuator and a second configuration, which prevents re-use with the actuator and prevents reinsertion of the cassette body into the actuator to an extent possible to enable actuation; and a carriage slidingly disposed within the cassette body, wherein each lockout clip has a first end fixed to an external surface of the cassette and a second end comprising a hook, wherein each hook is releasably engaged onto an inner surface of the carriage through an opening or window in the cassette body, prior to actuation.

2. The single use cassette assembly of claim 1 wherein the first configuration is a non-extended state and the second configuration is a naturally biased extended state.

3. The single use cassette assembly of claim 1; wherein the re-use prevention mechanism comprises two or four lock-out clips.

4. The single use cassette assembly of claim 1, wherein the cassette assembly further comprises the cassette body for engaging the actuator device and the carriage housed within the cassette body, the carriage having a channel configured to releasably retain a solid dose formulation.

5. The single use cassette assembly of claim 4, wherein the cassette body comprises a hook retaining edge for engaging the hook in the second configuration.

6. The single use cassette assembly of claim 4, wherein the carriage and cassette body comprise aligned apertures in which the lockout clips sit.

7. The single use cassette assembly of claim 4, wherein the one or more lockout clips remain in first a configuration or non-extended state until the cassette body is actuated forcing the one or more lockout clips to deflect outwardly to their second configuration or naturally biased extended state hooking the cassette body and preventing re-use of the cassette with the actuator.

8. The single use cassette assembly according to claim 4, wherein the one or more cassette lockout clips comprise spring steel sheet-metal or other shape-memory material.

9. The single use cassette assembly according to claim 4, wherein the cassette assembly further comprises a cassette pin positioned rearwardly from the solid dose, and wherein the cassette pin is temporarily secured by one or more pin release clips preventing any forward motion being transferred to the solid dose prior to actuation of the actuator.

10. The single use cassette assembly according to claim 9, wherein the carriage body further defines at least one or more pin clip windows, the one or more pin release clips being configured to deflect into the one or more pin clip windows to allow forward motion of the cassette pin within the carriage at the desired point during actuation.

11. The single use cassette assembly according to claim 4, wherein the carriage is releasably secured within the cassette body by one or more pre-release legs and wherein the pre-release legs are released when the cassette assembly is inserted into the actuator by a feature in the actuator mechanism.

12. The single use cassette assembly according to claim 4, wherein the carriage is adapted to be guided by rails within the cassette assembly and/or wherein the carriage comprises carriage jaws and a cassette opening cone.

13. The single use cassette assembly according to claim 4, wherein the cassette assembly further comprises a solid dose viewing window.

14. The single use cassette assembly according to claim 4, wherein the solid dose is a splinter or an implant and/or comprises a vaccine.

15. A kit comprising a solid dose needle-free delivery actuator and the single use cassette assembly according to claim 4.

16. The single use cassette assembly according to claim 1, wherein actuation of the cassette assembly releases the hook from the inner surface of the carriage, allowing the hook to visibly extend outwards following removal of the cassette assembly from the parenteral delivery actuator.

17. The single use cassette assembly according to claim 1, wherein the second configuration prevents reinsertion of the cassette assembly into the actuator to the same initial depth as prior to actuation.

18. The single use cassette assembly according to claim 1, wherein each hook is biased away from the carriage.

19. A single use cassette assembly for use with a parenteral delivery actuator and configured to allow operative connection therewith, the cassette assembly comprising: a re-use prevention mechanism including at least: a cassette body with one or more lockout clips having a first configuration, which permits use of the cassette body with the actuator, and a second configuration, which prevents re-use with the actuator and prevents reinsertion of the cassette body into the actuator to an extent possible to enable actuation; and a carriage slidingly disposed within the cassette body, wherein each lockout clip has a first end fixed to an external surface of the cassette body and a second end comprising a hook, wherein each hook is releasably engaged onto an inner surface of the carriage through an opening or window in the cassette body, prior to actuation, wherein actuation of the cassette assembly releases the hook from the inner surface of the carriage, allowing the hook to visibly extend outwards following removal of the cassette assembly from the parenteral delivery actuator, wherein the second configuration; prevents reinsertion of the cassette assembly into the actuator to the same initial depth as prior to actuation, and wherein each hook is biased away from the carriage.

* * * * *